(12) United States Patent
Sato

(10) Patent No.: US 6,178,227 B1
(45) Date of Patent: Jan. 23, 2001

(54) PORTABLE-TYPE FLUORESCENT X-RAY ANALYZER

(75) Inventor: Masao Sato, Chiba (JP)

(73) Assignee: Seiko Instruments Inc. (JP)

( * ) Notice: Under 35 U.S.C. 154(b), the term of this patent shall be extended for 0 days.

(21) Appl. No.: 09/293,091

(22) Filed: Apr. 16, 1999

(30) Foreign Application Priority Data

Apr. 17, 1998 (JP) .................................................. 10-108312

(51) Int. Cl.$^7$ ...................................................... H05G 1/54
(52) U.S. Cl. ............................................ 378/117; 378/114
(58) Field of Search ................................... 378/102, 114, 378/204, 160, 117, 50, 54, 59, 71, 48, 98

(56) References Cited

U.S. PATENT DOCUMENTS

| | | | |
|---|---|---|---|
| 2,297,042 | * 9/1942 | Weyenberg | 378/48 |
| 4,362,932 | * 12/1982 | Clark | 378/48 |
| 4,429,409 | * 1/1984 | Berry et al. | 378/48 |

* cited by examiner

Primary Examiner—David P. Porta
Assistant Examiner—Irakli Kiknadze

(74) Attorney, Agent, or Firm—Adams & Wilks

(57) ABSTRACT

An improved x-ray analyzer may be portable to permit on-site or outdoor analysis without the possibility of emitting harmful x-rays. A housing of the analyzer contains an x-ray generation system for generating x-rays and irradiating the x-rays onto a sample under analysis, an x-ray detection system for detecting x-rays emitted by the sample in response to irradiation of the sample by x-rays by the x-ray generation system, and a safety mechanism for permitting x-rays to be emitted from the housing only when a sample is under analysis. A normally-closed shutter is disposed between the x-ray generation system and a measurement window mounted to the housing through which x-rays are emitted. The safety mechanism includes a first switch which permits the shutter to be opened only when the housing is in contact with a sample under analysis so as to prevent the emission of x-rays from the housing when the housing is not in contact with a sample under analysis. The first switch is a pressure-actuated micro-switch mounted proximate the measurement window so as to become actuated when the measurement window is brought into contact with the sample under analysis to permit opening of the shutter. A hand grip is preferably mounted to the housing and has a second switch mounted thereto and actuatable when the hand grip is engaged by a user's hand to prevent opening of the shutter when the second switch is engaged.

28 Claims, 2 Drawing Sheets

PORTABLE-TYPE FLUORESCENT X-RAY ANALYZER

BACKGROUND OF THE INVENTION

The present invention relates to a portable-type fluorescent X-ray analyzer having principal purposes of elementary analysis conducted on site or outdoors for archaeological, evidential and criminal site searches or fire initial investigations.

Conventionally, in the case of conducting elementary analysis on site or outdoors, elementary analysis has been carried out on the vehicle after performing sampling with mounted on the vehicle a portable-type X-ray analyzer having a radio isotope as a radiation source or a small fluorescent X-ray analyzer such as a desktop type.

Conventionally, safety has been secured in the portable X-ray analyzer using providing radioisotope as a radiation source by only a shutter opening and closing, wherein the responsibility upon opening the shutter has been placed upon the operator. Also, such problems have arisen such as the need for exclusive-duty persons to remain in charge of handling the equipment in view of the use of radioisotope as well as difficulty in registration.

The method of mounting a desktop-type small fluorescent X-ray analyzer on a vehicle could realize the goal of conducting analysis nearby the site but could not implement analysis by stepping near to a sample impossible of sampling.

Although samples with proper hardness and thickness are fallen in the destructive type, but can be sampled by cutting or breaking with a saw or hammer, there have been cases that hard samples such as ultra high strength steels are difficult to perform such pre-treatments.

Meanwhile, in the case of a general fluorescent X-ray analyzer, because objects to be measured could be contained within a sample chamber structural body of a closed shield type, protection against leakage X-rays outside the apparatus were easy to implement. However, portable fluorescent analyzers for the purpose of outdoor use, they were made in full-open types with respect to a direction of X-ray radiation as a structure having high possibility of exposure to the X-ray.

SUMMARY OF THE INVENTION

An X-ray tube is employed in place of a radioisotope and safety is secured for shutter opening and closing operations by the various switches and sequences, thereby enabling fluorescent X-ray analysis outdoors with safety.

DETAILED DESCRIPTION OF THE INVENTION

Figure 1:
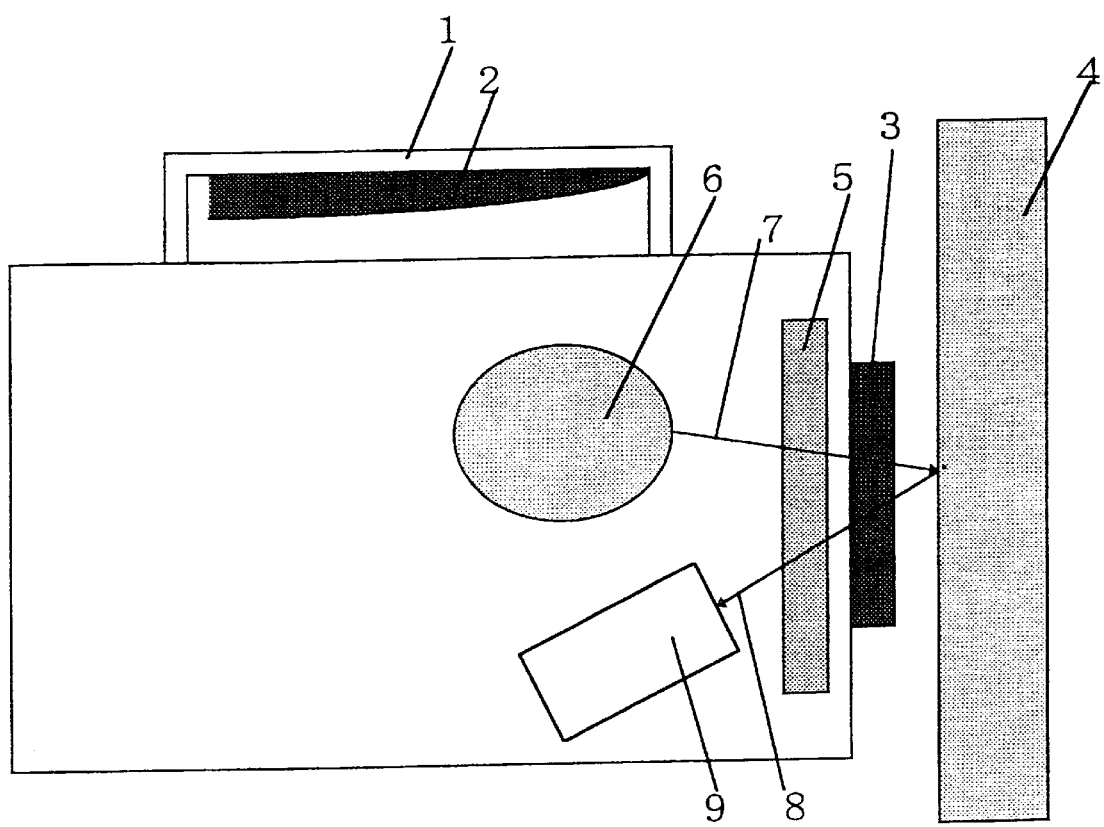
FIG. 1 shows an embodiment of arranging safety switches for a small portable fluorescent X-ray analyzer.

FIG. 1 shows an arrangement of safety switches for a fluorescent X-ray analyzer of a small portable type. During the usual carrying of the device, a lever-actuated micro-switch 2 of a hand grip 1 is grasped thereby turning a signal ON. When releasing the hand from the grip, the signal turns OFF. A pressure-actuated micro-switch 3 at a measuring section disposed at the front end of a casing, if contacted with a sample 4, causes a signal to turn ON during measurement. An OFF state is maintained while in non-contact with the sample 4. A shutter 5 closes an X-ray irradiation aperture, which is made up of a metal having a sufficient thickness to completely shield, during non-measurement, an X-ray inside a window at the measuring section front end, thus providing a structure free of X-ray leakage outside the casing. During measurement the shutter 5 is in an open state irradiating a primary X-ray 7 from an X-ray tube 6 to the sample 4, so that fluorescent X-rays 8 inherent to elements composing the sample 4 can be counted by an X-ray detector 9. In the present embodiment, the x-ray analyzer may be carried by hand to a site where the sample 4 exists outdoors x-rays are emitted, only when the casing measuring section front end is put in contact with a measuring position by which the micro-switch 3 is ON and the micro-switch 2 is OFF by releasing the hand from the grip, so that the shutter 5 open state is allowed to enable a measurement based on a principle of a fluorescent X-ray analytical method.

Figure 2:
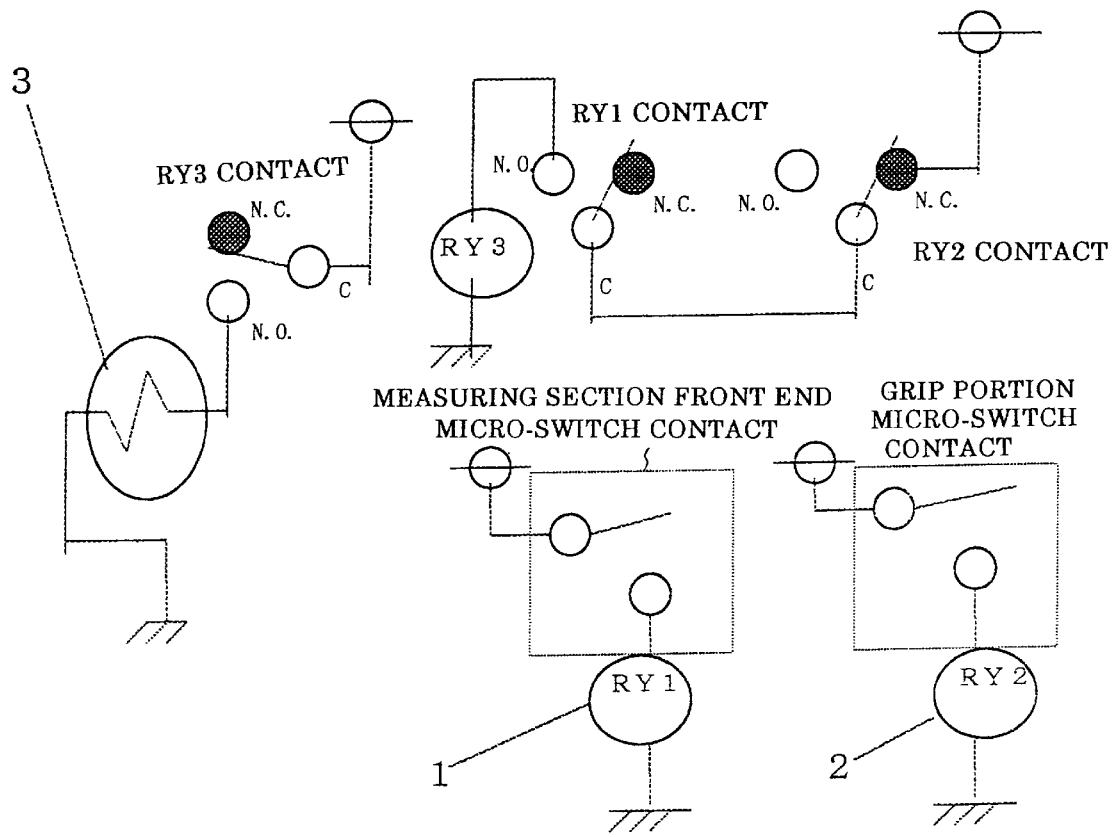
FIG. 2 shows a circuit embodiment.

FIG. 2 is a circuit embodiment example for realizing the above-described operation. Because the micro-switch on the grip is open, no current flaws through a coil of RY2. An RY2 contact is in a state in which C (common terminal) and N.C. (normally-closed terminal) are in contact with each other. On the other hand, when the micro-switch at the measuring section front end is in a closed state due to contact with the sample, a current flows through a coil of RY1 so that a contact of RY1 is in a state wherein C (common terminal) and N.O. (normal open terminal) are in contact with each other. As a result a current is caused to flow through a coil of RY3. Accordingly, a contact of RY3 is in a state in which C and N.O. are in contact with each other, supplying a current to a solenoid 3 and hence opening the shutter.

With safety against X-ray leakage ensured, elementary analysis can be on site outdoors without encountering worsening in operationality.

What is claimed is:

1. In a portable fluorescent x-ray analyzer having an x-ray generating system and an x-ray detecting system disposed in a housing for conducting x-ray analysis using a fluorescent x-ray method, safety means for preventing the emission of x-rays comprising: a first switch disposed proximate a measurement window of the housing of the portable fluorescent x-ray analyzer for detecting contact with an object to be analyzed and outputting a first signal when such contact is detected, a second switch disposed proximate a hand grip used for carrying the housing for detecting when the hand grip is engaged by a user's hand and outputting a second signal when the hand grip is so engaged, and an electric circuit for permitting the emission of an x-ray from the housing by the x-ray generating system only when the first signal is being output and the second signal is not being output.

2. A portable fluorescent x-ray analyzer according to claim 1; wherein the x-ray generating system comprises an x-ray tube disposed in the housing for emitting x-rays through a window located at a first end of the housing, and the x-ray detecting system comprises an x-ray detector disposed in the housing for detecting fluorescent x-rays reflected by the object through the window.

3. A portable fluorescent x-ray analyzer according to claim 1; wherein the x-ray generating system does not employ a radioisotope.

4. A portable fluorescent x-ray analyzer according to claim 1; wherein the first switch comprises a pressure-actuated micro-switch mounted at a first end of the housing through which x-rays are emitted, so that the first switch becomes actuated when the first end of the housing is brought into contact with the object to be analyzed so as to output the first signal.

5. A portable fluorescent x-ray analyzer according to claim 4; wherein the first switch comprises a normally-open switch.

6. A portable fluorescent x-ray analyzer according to claim 1; wherein the second switch comprises a lever-actuated micro-switch mounted to the hand grip so that contact by the user's hand while the user is holding or carrying the housing causes the lever to actuate the micro-switch to output the second signal so as to prevent an x-ray from being emitted from the housing.

7. A portable fluorescent x-ray analyzer according to claim 6; wherein the second switch comprises a normally-closed switch which becomes open only when the user is holding or carrying the housing by the hand grip so as to prevent an x-ray from being emitted from the housing.

8. A portable fluorescent x-ray analyzer according to claim 1; further comprising a normally-closed shutter disposed between the x-ray generating system and a window mounted to the housing through which x-rays are emitted, the opening and closing of the shutter being controlled by the electric circuit so as to become open only when the first signal is being output and the second signal is not being output.

9. A portable fluorescent x-ray analyzer comprising: a housing; a hand grip mounted to the housing; an x-ray generating system disposed in the housing for generating x-rays; a fluorescent x-ray detecting system disposed in the housing for detecting fluorescent x-rays projected into the housing; a measurement window mounted to the housing through which x-rays emitted by the x-ray generating system may pass and through which fluorescent x-rays emitted by a sample under analysis may pass, so that x-ray analysis may be conducted; a shutter mounted to the housing for preventing x-rays from being emitted from the housing when in a closed state and for permitting x-rays to be emitted from the housing when in an open state; and a safety mechanism for controlling operation of the shutter so that the shutter remains in a closed state at all times when the housing is not in contact with a sample under analysis.

10. A portable fluorescent x-ray analyzer according to claim 9; wherein the x-ray generating system comprises an x-ray tube disposed in the housing for projecting x-rays through the measurement window onto a sample under analysis.

11. A portable fluorescent x-ray analyzer according to claim 9; wherein the fluorescent x-ray detecting system comprises an x-ray detector disposed in the housing for detecting fluorescent x-rays emitted by a sample under analysis in response to the projection x-rays thereon by the x-ray generating system.

12. A portable fluorescent x-ray analyzer according to claim 9; wherein the x-ray generating system does not employ a radioisotope.

13. A portable fluorescent x-ray analyzer according to claim 9; wherein the safety mechanism comprises a first switch disposed proximate the measurement window for detecting contact between a portion of the housing and a sample under analysis and outputting a first signal when such contact is detected, and a circuit receptive of the first signal to permit opening of the shutter.

14. A portable fluorescent x-ray analyzer according to claim 13; wherein the first switch comprises a pressure-actuated micro-switch mounted proximate the measurement window so that the first switch becomes actuated when the measurement window is brought into contact with the sample under analysis.

15. A portable fluorescent x-ray analyzer according to claim 14; wherein the first switch comprises a normally-open switch.

16. A portable fluorescent x-ray analyzer according to claim 9; wherein the safety mechanism further comprises a second switch mounted to the hand grip for detecting when the grip is engaged by a user's hand and outputting a second signal when the grip is so engaged, and wherein the circuit is receptive of the second signal to prevent opening of the shutter when the second signal is being output.

17. A portable fluorescent x-ray analyzer according to claim 16; wherein the second switch comprises a lever-actuated micro-switch mounted to the hand grip so that contact by the user's hand while the user is holding or carrying the housing causes the lever to actuate the micro-switch to output the second signal so as to prevent x-rays from being emitted from the housing.

18. A portable fluorescent x-ray analyzer according to claim 17; wherein the second switch comprises a normally-closed switch which becomes open only when the user is holding or carrying the housing by the grip so as to prevent x-rays from being emitted from the housing.

19. An x-ray analyzer comprising: a housing; an x-ray generation system for generating x-rays and irradiating the x-rays onto a sample under analysis; an x-ray detection system for detecting x-rays emitted by the sample in response to irradiation of the sample by x-rays by the x-ray generation system; and a safety mechanism for permitting x-rays to be emitted from the housing only when a sample is under analysis.

20. An x-ray analyzer according to claim 19; further comprising a normally-closed shutter disposed between the x-ray generation system and a measurement window mounted to the housing through which x-rays are emitted; and wherein the safety mechanism includes a first switch which permits the shutter to be opened only when the housing is in contact with a sample under analysis so as to prevent the emission of x-rays from the housing when the housing is not in contact with a sample under analysis.

21. An x-ray analyzer according to claim 20; wherein the first switch comprises a pressure-actuated micro-switch mounted proximate the measurement window so that the first switch becomes actuated when the measurement window is brought into contact with the sample under analysis to permit opening of the shutter.

22. An x-ray analyzer according to claim 21; wherein the first switch comprises a normally-open switch.

23. An x-ray analyzer according to claim 20; further comprising a hand grip mounted to the housing; and wherein the safety mechanism further comprises a second switch mounted to the hand grip and actuatable when the grip is engaged by a user's hand to prevent opening of the shutter when the second switch is engaged.

24. An x-ray analyzer according to claim 23; wherein the second switch comprises a lever-actuated micro-switch mounted to the hand grip so that contact by the user's hand while the user is holding or carrying the housing causes the lever to actuate the micro-switch to prevent x-rays from being emitted from the housing.

25. An x-ray analyzer according to claim 24; wherein the second switch comprises a normally-closed switch which becomes open only when the user is holding or carrying the housing by the grip so as to prevent x-rays from being emitted from the housing.

26. An x-ray analyzer according to claim 19; wherein the x-ray generating system comprises an x-ray tube disposed in the housing for projecting x-rays through the measurement window onto a sample under analysis.

27. An x-ray analyzer according to claim 19; wherein the fluorescent x-ray detecting system comprises an x-ray detector disposed in the housing for detecting fluorescent x-rays emitted by a sample under analysis in response to the projection x-rays thereon by the x-ray generating system.

28. An x-ray analyzer according to claim 19; wherein the x-ray generating system does not employ a radioisotope.

* * * * *